United States Patent [19]
Fukuta et al.

[11] Patent Number: 6,051,406
[45] Date of Patent: Apr. 18, 2000

[54] KERATAN SULFATE 6-SULFOTRANSFERASE AND DNA CODING FOR THE SAME

[75] Inventors: Masakazu Fukuta, Mie-ken; Osami Habuchi, Nagoya, both of Japan

[73] Assignee: Seikagaku Kogyo Kabushiki Kaish, Tokyo, Japan

[21] Appl. No.: 08/980,659

[22] Filed: Dec. 1, 1997

[30] Foreign Application Priority Data

Nov. 29, 1996 [JP] Japan ..................................... 8-320535

[51] Int. Cl.7 ............................. C12N 9/10; C12N 15/54; C12P 19/12
[52] U.S. Cl. ............................ 435/101; 435/97; 435/193; 536/23.2
[58] Field of Search ............................. 435/193, 97, 101; 536/23.2

[56] References Cited

FOREIGN PATENT DOCUMENTS 0 745 668 A2  12/1996  European Pat. Off. .

OTHER PUBLICATIONS

E.R. Rüter et al. "Partial Purification and Characterization of 3'–Phosphoadenylylsulfate:Keratan Sulfate Sulfotransferases", Biol Chem. 259(19): 11771–11776, Oct. 1984.

Hirofumi Inoue, et al., Glycosaminoglycan Sulfotransferases in Human and Animal Sera, The Journal of Biological Chemistry, vol. 261, No. 10, Issue of Apr. 5, pp. 4460–4469, 1986.

Kazuyuki Sugahara, et al., Paper Disk Assay for Glycosaminoglycan Sulfotransferases, Analytical Biochemistry 166, 404–412 Apr. 1987.

Kazuyuki Sugihara et al., Developmental Changes in Glycosaminoglycan Sulfotransferase Activities in Animal Snear, Archives of Biochemistry and Biophysics, vol. 258, No. 2, Nov. 1, pp. 391–403, 1987.

Kazuyuki Sugahara, et al., Regulation of Serum Glycosaminoglycan Sulfotransferase Activities; Inhibition by Sulfated Glycosaminoglycans and Activation by Polyamines and Basic Peptides Including a Polylysine–Containing Segment of the c–Ki–ras 2 Protein, J. Biochem. 106, 910–919 (1989).

Fukuta et al., Molecular Cloning and Expression of Chick Chondrocyte Chondroitin 6–Sulfotransferase J. Bio. Chem 270(31): 18575–18580, Aug. 1995.

K.J. Williams, "Atherosclerosis: Cell Biology and Lipoproteins", Curr. Opin, Lipidol. 7(6): U202–U208, Dec. 1996.

Fukuta et al., Molecular Cloning and Expression of Human Chondroitin 6–Sulfotransferase Biochim. Biophys. Acta 1399: 57–61, Jul. 1998.

Kiyoshi Nakazawa, et al., J. Biochem. vol. 117, 1995, pp. 707–718, Proteoglycan Synthesis by Corneal Explants from Developing Embryonic Chicken.

Masakazu Fukuta, et al. The Journal of Biological Chemistry vol. 272 No. 51, Dec. 19, 1997, pp. 32321–32328, Molecular Cloning and Characterization of Human Keratan Sulfate Gal–6–Sulfotransferase.

*Primary Examiner*—Rebecca Prouty
*Attorney, Agent, or Firm*—Knobbe, Martens, Olson & Bear, LLP

[57] ABSTRACT

A polypeptide of keratan sulfate 6-sulfotransferase having the following physicochemical properties:

① action: a sulfate group is transferred from a sulfate group donor to the hydroxyl group at C-6 position of galactose residue of keratan sulfate;

② substrate specificity: a sulfate group is not substantially transferred to chondroitin, chondroitin sulfate A, chondroitin sulfate C, dermatan sulfate and CDSNS-heparin;

③ optimum pH: 6.2 to 6.5

④ activation: an activity is increased by $Mn^{2+}$ or $Ca^{2+}$;

⑤ Km value for 3'-phosphoadenosine 5'-phosphosulfate: about $2 \times 10^{-7}$ M; and a DNA coding for the polypeptide.

8 Claims, 3 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1458
      (B) TYPE: nucleic acid
      (C) STRANDEDNESS: both
      (D) TOPOLOGY: linear (ii) MOLECULE TYPE: cDNA (vi) ORIGINAL SOURCE:
      (A) ORGANISM: Human
      (B) TISSUE TYPE: Fetal brain (ix) FEATURE:
        NAME/KEY: CDS
        LOCATION: 1..1233

(xi) SEQUENCE DESCRIPTION: SEQ ID NO:1:

```
ATG CAA TGT TCC TGG AAG GCC GTC CTC CTC CTT GCC CTG GCC TCC ATT      48
Met Gln Cys Ser Trp Lys Ala Val Leu Leu Leu Ala Leu Ala Ser Ile
 1               5                  10                  15

GCC ATC CAG TAC ACG GCC ATC CGC ACC TTC ACC GCC AAG TCC TTT CAC      96
Ala Ile Gln Tyr Thr Ala Ile Arg Thr Phe Thr Ala Lys Ser Phe His
             20                  25                  30

ACC TGC CCC GGG CTG GCA GAG GCC GGG CTG GCC GAG CGA CTG TGC GAG     144
Thr Cys Pro Gly Leu Ala Glu Ala Gly Leu Ala Glu Arg Leu Cys Glu
         35                  40                  45

GAG AGC CCC ACC TTC GCC TAC AAC CTC TCC CGC AAG ACC CAC ATC CTC     192
Glu Ser Pro Thr Phe Ala Tyr Asn Leu Ser Arg Lys Thr His Ile Leu
     50                  55                  60

ATC CTG GCC ACC ACG CGC AGC GGC TCC TCC TTC GTG GGC CAG CTC TTC     240
Ile Leu Ala Thr Thr Arg Ser Gly Ser Ser Phe Val Gly Gln Leu Phe
 65                  70                  75                  80

AAC CAG CAC CTG GAC GTC TTC TAC CTG TTT GAG CCC CTC TAC CAC GTC     288
Asn Gln His Leu Asp Val Phe Tyr Leu Phe Glu Pro Leu Tyr His Val
                 85                  90                  95

CAG AAC ACG CTC ATC CCC CGC TTC ACC CAG GGC AAG AGC CCG GCC GAC     336
Gln Asn Thr Leu Ile Pro Arg Phe Thr Gln Gly Lys Ser Pro Ala Asp
            100                 105                 110

CGG CGG GTC ATG CTA GGC GCC AGC CGC GAC CTC CTG CGG AGC CTC TAC     384
Arg Arg Val Met Leu Gly Ala Ser Arg Asp Leu Leu Arg Ser Leu Tyr
        115                 120                 125

GAC TGC GAC CTC TAC TTC CTG GAG AAC TAC ATC AAG CCG CCG CCG GTC     432
Asp Cys Asp Leu Tyr Phe Leu Glu Asn Tyr Ile Lys Pro Pro Pro Val
    130                 135                 140
```

```
AAC CAC ACC ACC GAC AGG ATC TTC CGC CGC GGG GCC AGC CGG GTC CTC      480
Asn His Thr Thr Asp Arg Ile Phe Arg Arg Gly Ala Ser Arg Val Leu
145                 150                 155                 160

TGC TCC CGG CCT GTG TGC GAC CCT CCG GGG CCA GCC GAC CTG GTC CTG      528
Cys Ser Arg Pro Val Cys Asp Pro Pro Gly Pro Ala Asp Leu Val Leu
                165                 170                 175

GAG GAG GGG GAC TGT GTG CGC AAG TGC GGG CTA CTC AAC CTG ACC GTG      576
Glu Glu Gly Asp Cys Val Arg Lys Cys Gly Leu Leu Asn Leu Thr Val
            180                 185                 190

GCG GCC GAG GCG TGC CGC GAG CGC AGC CAC GTG GCC ATC AAG ACG GTG      624
Ala Ala Glu Ala Cys Arg Glu Arg Ser His Val Ala Ile Lys Thr Val
        195                 200                 205

CGC GTG CCC GAG GTG AAC GAC CTG CGC GCC CTG GTG GAA GAC CCG CGA      672
Arg Val Pro Glu Val Asn Asp Leu Arg Ala Leu Val Glu Asp Pro Arg
210                 215                 220

TTA AAC CTC AAG GTC ATC CAG CTG GTC CGA GAC CCC CGC GGC ATT CTG      720
Leu Asn Leu Lys Val Ile Gln Leu Val Arg Asp Pro Arg Gly Ile Leu
225                 230                 235                 240

GCT TCG CGC AGC GAG ACC TTC CGC GAC ACG TAC CGG CTC TGG CGG CTC      768
Ala Ser Arg Ser Glu Thr Phe Arg Asp Thr Tyr Arg Leu Trp Arg Leu
                245                 250                 255

TGG TAC GGC ACC GGG AGG AAA CCC TAC AAC CTG GAC GTG ACG CAG CTG      816
Trp Tyr Gly Thr Gly Arg Lys Pro Tyr Asn Leu Asp Val Thr Gln Leu
            260                 265                 270

ACC ACG GTG TGC GAG GAC TTC TCC AAC TCC GTG TCC ACC GGC CTC ATG      864
Thr Thr Val Cys Glu Asp Phe Ser Asn Ser Val Ser Thr Gly Leu Met
        275                 280                 285

CGG CCC CCG TGG CTC AAG GGC AAG TAC ATG TTG GTG CGC TAC GAG GAC      912
Arg Pro Pro Trp Leu Lys Gly Lys Tyr Met Leu Val Arg Tyr Glu Asp
290                 295                 300

CTG GCT CGG AAC CCT ATG AAG AAG ACC GAG GAG ATC TAC GGG TTC CTG      960
Leu Ala Arg Asn Pro Met Lys Lys Thr Glu Glu Ile Tyr Gly Phe Leu
305                 310                 315                 320

GGC ATC CCG CTG GAC AGC CAC GTG GCC CGC TGG ATC CAG AAC AAC ACG     1008
Gly Ile Pro Leu Asp Ser His Val Ala Arg Trp Ile Gln Asn Asn Thr
                325                 330                 335

CGG GGC GAC CCC ACC CTG GGC AAG CAC AAA TAC GGC ACC GTG CGA AAC     1056
Arg Gly Asp Pro Thr Leu Gly Lys His Lys Tyr Gly Thr Val Arg Asn
            340                 345                 350

TCG GCG GCC ACG GCC GAG AAG TGG CGC TTC CGC CTC TCC TAC GAC ATC     1104
Ser Ala Ala Thr Ala Glu Lys Trp Arg Phe Arg Leu Ser Tyr Asp Ile
        355                 360                 365

GTG GCC TTT GCC CAG AAC GCC TGC CAG CAG GTG CTG GCC CAG CTG GGC     1152
Val Ala Phe Ala Gln Asn Ala Cys Gln Gln Val Leu Ala Gln Leu Gly
370                 375                 380

TAC AAG ATC GCC GCC TCG GAG GAG GAG CTG AAG AAC CCC TCG GTC AGC     1200
Tyr Lys Ile Ala Ala Ser Glu Glu Glu Leu Lys Asn Pro Ser Val Ser
385                 390                 395                 400

CTG GTG GAG GAG CGG GAC TTC CGC CCC TTC TCG TGACCCGGGC GGTGCGGGTG   1253
Leu Val Glu Glu Arg Asp Phe Arg Pro Phe Ser
                405                 410

GGGGCGGGAG GCGCAAGGTG TCGGTTTTGA TAAAATGGAC CGTTTTTAAC TGTTGCCTTA   1313

TTAACCCCTC CCTCTCCCAC CTCATCTTCG TGTCCTTCCT GCCCCAGCT CACCCCACTC    1373

CCTTCTGCCC CTTTTTTGTC TCTGAAATTT GCACTACGTC TTGGACGGGA ATCACTGGGG   1433

CAGAGGGCGC CTGAAGTAGG GTCCC                                        1458
```

(2) INFORMATION FOR SEQ ID NO:2:

(i) SEQUENCE CHARACTERISTICS:
    (A) LENGTH: 411
    (B) TYPE: amino acid
    (D) TOPOLOGY: linear (ii) MOLECULE TYPE: peptide (xi) SEQUENCE DESCRIPTION: SEQ ID NO:2:

```
Met Gln Cys Ser Trp Lys Ala Val Leu Leu Ala Leu Ala Ser Ile
1               5                   10                  15

Ala Ile Gln Tyr Thr Ala Ile Arg Thr Phe Thr Ala Lys Ser Phe His
            20                  25                  30

Thr Cys Pro Gly Leu Ala Glu Ala Gly Leu Ala Glu Arg Leu Cys Glu
            35                  40                  45

Glu Ser Pro Thr Phe Ala Tyr Asn Leu Ser Arg Lys Thr His Ile Leu
        50                  55                  60

Ile Leu Ala Thr Thr Arg Ser Gly Ser Ser Phe Val Gly Gln Leu Phe
65                  70                  75                  80

Asn Gln His Leu Asp Val Phe Tyr Leu Phe Glu Pro Leu Tyr His Val
                85                  90                  95

Gln Asn Thr Leu Ile Pro Arg Phe Thr Gln Gly Lys Ser Pro Ala Asp
            100                 105                 110

Arg Arg Val Met Leu Gly Ala Ser Arg Asp Leu Leu Arg Ser Leu Tyr
            115                 120                 125

Asp Cys Asp Leu Tyr Phe Leu Glu Asn Tyr Ile Lys Pro Pro Val
130                 135                 140

Asn His Thr Thr Asp Arg Ile Phe Arg Arg Gly Ala Ser Arg Val Leu
145                 150                 155                 160

Cys Ser Arg Pro Val Cys Asp Pro Pro Gly Pro Ala Asp Leu Val Leu
                165                 170                 175

Glu Glu Gly Asp Cys Val Arg Lys Cys Gly Leu Leu Asn Leu Thr Val
                180                 185                 190

Ala Ala Glu Ala Cys Arg Glu Arg Ser His Val Ala Ile Lys Thr Val
            195                 200                 205

Arg Val Pro Glu Val Asn Asp Leu Arg Ala Leu Val Glu Asp Pro Arg
            210                 215                 220

Leu Asn Leu Lys Val Ile Gln Leu Val Arg Asp Pro Arg Gly Ile Leu
225                 230                 235                 240

Ala Ser Arg Ser Glu Thr Phe Arg Asp Thr Tyr Arg Leu Trp Arg Leu
                245                 250                 255

Trp Tyr Gly Thr Gly Arg Lys Pro Tyr Asn Leu Asp Val Thr Gln Leu
            260                 265                 270

Thr Thr Val Cys Glu Asp Phe Ser Asn Ser Val Ser Thr Gly Leu Met
            275                 280                 285

Arg Pro Pro Trp Leu Lys Gly Lys Tyr Met Leu Val Arg Tyr Glu Asp
            290                 295                 300

Leu Ala Arg Asn Pro Met Lys Leu Thr Glu Glu Ile Tyr Gly Phe Leu
305                 310                 315                 320

Gly Ile Pro Leu Asp Ser His Val Ala Arg Trp Ile Gln Asn Thr
                325                 330                 335

Arg Gly Asp Pro Thr Leu Gly Lys His Lys Tyr Gly Thr Val Arg Asn
            340                 345                 350

Ser Ala Ala Thr Ala Glu Lys Trp Arg Phe Arg Leu Ser Tyr Asp Ile
            355                 360                 365
```

```
-continued

Val Ala Phe Ala Gln Asn Ala Cys Gln Val Leu Ala Gln Leu Gly
    370                 375                 380

Tyr Lys Ile Ala Ala Ser Glu Glu Leu Lys Asn Pro Ser Val Ser
385                 390                 395                 400

Leu Val Glu Glu Arg Asp Phe Arg Pro Phe Ser
                405             410
```

KERATAN SULFATE 6-SULFOTRANSFERASE AND DNA CODING FOR THE SAME

BACKGROUND OF THE INVENTION

The present invention relates to a polypeptide of glycosaminoglycan sulfotransferase (glycosaminoglycan sulfate group transferase) and a DNA coding for it. More particularly, the present invention relates to a polypeptide of 6-sulfotransferase originating from human, which sulfates keratan sulfate, but substantially does not sulfate chondroitin, chondroitin sulfate A, chondroitin sulfate C, dermatan sulfate and CDSNS-heparin, and a DNA coding for it. The present invention further relates to a method for the preparation of the polypeptide and a method for using the polypeptide of 6-sulfotransferase.

Keratan sulfate is a kind of glycosaminoglycan constituted by galactose residues (Gal), and N-acetylglucosamine residues (GlcNAc) a part of which has substituents of sulfate groups at the C-6 position, and its repetition structure is represented by 3Galβ1→4GlcNAcβ1→.

It is expected that, if a gene for sulfotransferase for glycosaminoglycan could be cloned, it would provide information about substrate specificity of its receptors and approaches useful for structural and functional investigation of glycosaminoglycan. Various glycosaminoglycan sulfotransferases seem to be involved in the synthesis of glycosaminoglycan. However, it is difficult to clone a cDNA of sulfotransferase.

The present inventors had already purified apparently homogeneously chondroitin 6-sulfotransferase (it may be referred to as "C6ST" hereinafter), which transfers a sulfate group from 3'-phosphoadenosine 5'-phosphosulfate to the hydroxyl group at C-6 position of N-acetylgalactosamine residue of glycosaminoglycans such as chondroitin, from serum-free chick chondrocyte culture supernatant (Habuchi, O., Matsui, Y., Kotoya, Y., Aoyama, Y., Yasuda, Y., and Noda, M. (1993) J. Biol. Chem. 268, 21968–21974). Moreover, from its partial amino acid sequence, they had prepared an oligonucleotide primer, cloned a chick cDNA, and demonstrated that the polypeptide resulting from the DNA exhibited the C6ST activity. Furthermore, they also found that the enzyme could exhibit activity for transferring sulfate groups to the hydroxyl group at C-6 positions of galactose residues of keratan sulfate (Fukuta, M., Uchimura., K., Nakashima, K., Kato, M., Kimata, K., Shinomura, T., and Habuchi, O. (1995) J. Biol. Chem. 270, 18575–18580).

However, any DNA coding for a polypeptide of sulfotransferase that sulfates only keratan sulfate among chondroitins and keratan sulfate, i.e., sulfotransferase specific for keratan sulfate has not been reported. In particular, such a sulfotransferase originating from human and hence expected to be useful for pharmaceuticals has never been reported.

An enzyme which specifically transfers a sulfate group to keratan sulfate is important in functional studies of keratan sulfate. In particular, such an enzyme of human origin is very important for providing keratan sulfates in order to create pharmaceuticals exhibiting physiological activity preferred for humans. Furthermore, if a DNA coding for a polypeptide of keratan sulfate 6-sulfotransferase originating from human is obtained, it may be expected to be used for therapeutic drugs including those for gene therapy or diagnostic drugs for human diseases caused by, for example, low sulfation of galactose residues of keratan sulfate at their C-6 positions ("low sulfation" herein used means that sulfation degree is low).

The enzyme which specifically transfers a sulfate group to keratan sulfate is expected to be used for the syntheses of GlyCAM-1 (highly glycosylated cell adhesion molecule-1, glycosylation-dependent cell adhesion molecule-1, expected to be used as an antiinflammatory agent), which is considered as one of ligands for L-selectin involved in homing of lymphocytes and rolling of leucocytes occurring during an early phase of inflammation, and sulfated lactosamine oligosaccharides. The DNA coding for this enzyme is also expected to be used for the production of the enzyme in a large scale and in vivo synthesis of GlyCAM-1 by gene transfer.

SUMMARY OF THE INVENTION

An object of the present invention is to provide a polypeptide and a partial polypeptide of glycosaminoglycan sulfotransferase specific for keratan sulfate and a DNA coding for the polypeptides. Another object of the present invention is to provide a method for the preparation of the polypeptides and a method for using the glycosaminoglycan sulfotransferase.

The present inventors have cloned a cDNA coding for chick chondroitin 6-sulfotransferase, and by using a fragment derived from the chick cDNA successfully cloned a cDNA coding for glycosaminoglycan 6-sulfotransferase that sulfates galactose residues of keratan sulfate but substantially does not sulfate chondroitins (referred to as "KSGal6ST" hereinafter) from human cDNA library. Therefore, the present invention provides a polypeptide of KSGal6ST or a part thereof (generically referred to as "polypeptide of the present invention" hereinafter), and a DNA coding for at least a part of human KSGal6ST (referred to as "DNA of the present invention" hereinafter).

The polypeptide of the present invention may be a polypeptide of keratan sulfate 6-sulfotransferase exhibiting the following physicochemical properties:

① action: a sulfate group is transferred from a sulfate group donor to the hydroxyl group at C-6 position of galactose residue of keratan sulfate;

② substrate specificity: a sulfate group is not substantially transferred to chondroitin, chondroitin sulfate A, chondroitin sulfate C, dermatan sulfate and CDSNS-heparin;

③ optimum pH: 6.2 to 6.5

④ activation: an activity is increased by $Mn^{2+}$ or $Ca^{2+}$;

⑤ Km value for 3'-phosphoadenosine 5'-phosphosulfate: about $2 \times 10^{-7}$ M The polypeptide of the present invention may be a polypeptide of 6-sulfotransferase which selectively sulfates C-6 positions of galactose residues of keratan sulfate and comprises at least a part of the amino acid sequence shown in SEQ ID NO: 2, which may include deletion, substitution or addition of one or more amino acids which substantially does not impair the 6-sulfotransferase activity for sulfating keratan sulfate. The polypeptide is preferably a polypeptide of 6-sulfotransferase which selectively sulfates C-6 positions of galactose residues of keratan sulfate and comprises at least a part of the amino acid sequence shown in SEQ ID NO: 2. More preferably, it is a polypeptide comprising at least a part of an amino acid sequence represented by amino acids 1–411 of SEQ ID NO: 2.

The polypeptide of the present invention may also be a polypeptide containing a portion of the polypeptides mentioned above.

The polypeptide of the present invention may be a polypeptide fused with another polypeptide.

The DNA of the present invention is a DNA coding for at least a part of the above polypeptides. Preferably, it has a nucleotide sequence coding for the amino acid sequence represented by the amino acids 1 to 411 of SEQ ID NO: 2, and more preferably, it comprises a part or all of a nucleotide sequence represented by the nucleotides 1 to 1233 of SEQ ID NO: 1.

The present invention also provides a method for the preparation of the polypeptide of the present invention comprising culturing cells harboring the DNA of the present invention in a suitable culture medium so that a polypeptide coded by the DNA is produced and accumulated in the culture, and collecting the polypeptide from the culture, and a method for producing a sulfated polysaccharide, comprising exposing keratan sulfate to the above polypeptide of 6-sulfotransferase.

According to the present invention, there are provided a DNA coding for human keratan sulfate 6-sulfotransferase (KSGal6ST) which transfers a sulfate group to the hydroxyl group at C-6 position of galactose residue of keratan sulfate, and a polypeptide expressed by a DNA fragment derived from the DNA.

Since a DNA coding for human KSGal6ST is provided by the present invention, it is expected that human KSGal6ST could be produced in such a large scale that industrial use of human KSGal6ST could be realized. The uses of the DNA of human KSGal6ST and KSGal6ST enzyme protein for pharmaceuticals are also expected.

DETAILED DESCRIPTION OF THE INVENTION

Figure 1:
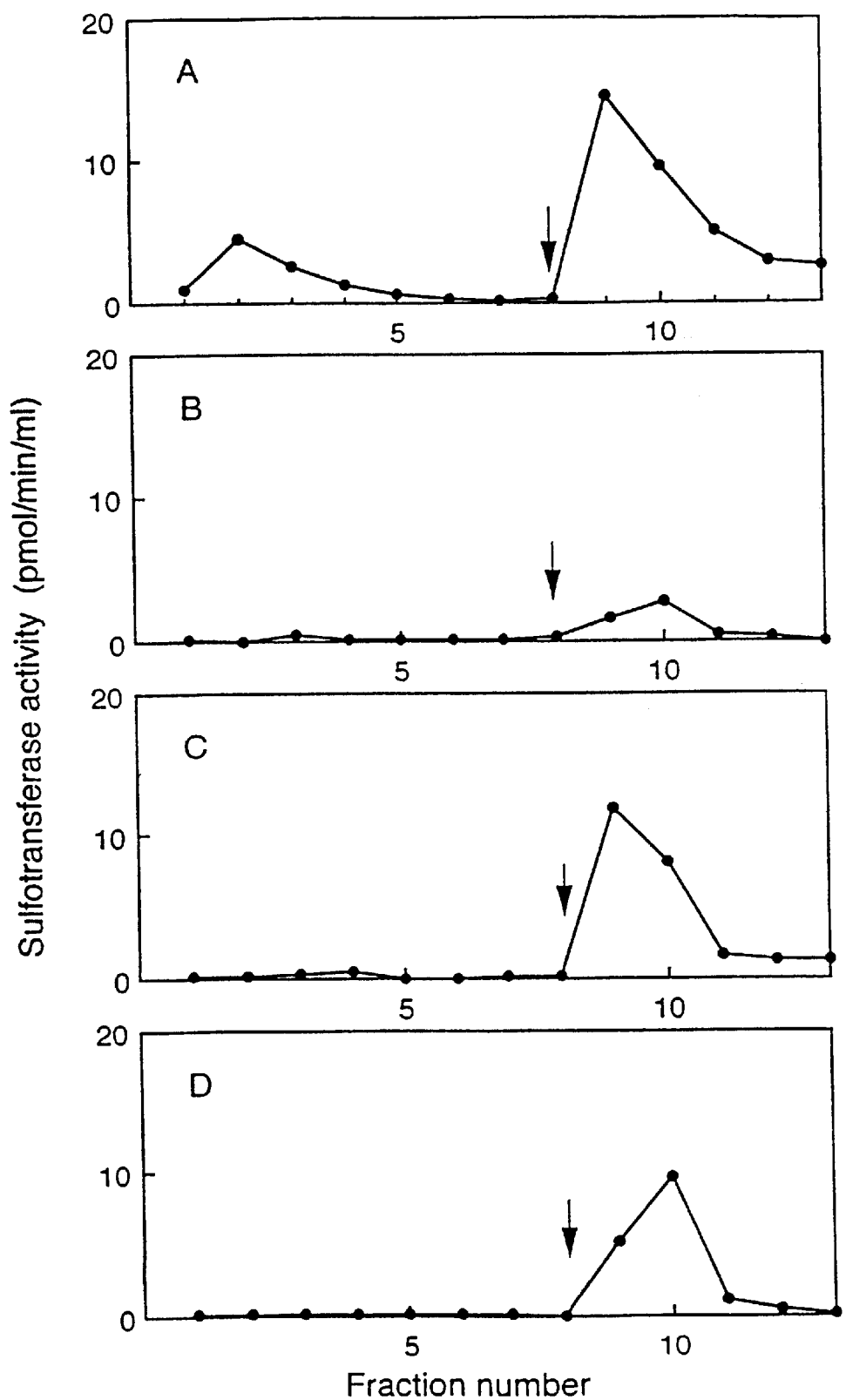
FIGS. 1A–1D show the results of DEAE-Sephacel column chromatography. A and C represent the elution profiles of extracts of COS-7 cells with pCXNKSST introduced, and B and D for the extracts of control COS-7 cells. A and B represent KSST activity, and C and D represent CST activity.

The present invention will be further described in detail regarding to the polypeptide of the present invention, the method for the preparation of the polypeptide of the present invention, the DNA of the present invention and the method for the preparation of the sulfated polysaccharide in this order.

<1> Polypeptide of the present invention

The polypeptide of the present invention may be a polypeptide of keratan sulfate 6-sulfotransferase having the following physicochemical properties:

① action: a sulfate group is transferred from a sulfate group donor to the hydroxyl group at C-6 position of galactose residue of keratan sulfate;

② substrate specificity: a sulfate group is not substantially transferred to chondroitin, chondroitin sulfate A, chondroitin sulfate C, dermatan sulfate and CDSNS-heparin (CDSNS-heparin refers completely desulfated N-sulfated heparin, prepared by completely desulfated heparin and sulfating it);

③ optimum pH: 6.2 to 6.5

④ activation: an activity is increased by $Mn^{2+}$ or $Ca^{2+}$;

⑤ Km value for sulfate group donor (3'-phosphoadenosine 5'-phosphosulfate): about $2\times10^{-7}$ M As the sulfate group donor mentioned above, 3'-phosphoadenosine 5'-phosphosulfate is preferred.

The polypeptide of the present invention may also be a polypeptide of 6-sulfotransferase which selectively sulfates C-6 position of galactose residues of keratan sulfate and comprises at least a part of the amino acid sequence shown in SEQ ID NO: 2, which may contain deletion, substitution or addition of one or more amino acids which substantially does not impair the 6-sulfotransferase activity for sulfating keratan sulfate.

That is, it may be a polypeptide of 6-sulfotransferase which selectively sulfates C-6 position of galactose residues of keratan sulfate and comprises at least a part of the following amino acid sequence (a) or (b):

(a) the amino acid sequence shown in SEQ ID NO: 2,
(b) an amino acid sequence of (a) having deletion, substitution or addition of one or more amino acids which substantially do not impair the 6-sulfotransferase activity for sulfating keratan sulfate.

Such deletion, substitution or addition of one or more amino acids can be obtained by introducing deletion, substitution or addition of nucleotides which may cause deletion, substitution or addition of one or more amino acids into a DNA coding for at least a part of the sequence of SEQ ID NO: 2 and expressing the resulting DNA. Such introduction of deletion, substitution or addition of nucleotides into a DNA sequence can be made by synthesizing a sequence containing a mutated sequence and restriction sites at the both ends, and replacing a corresponding portion of an unmutated sequence with the synthesized sequence. Deletion, substitution or addition can also be introduced into a DNA sequence by the site-directed mutagenesis (Kramer, W. and Frits, H. J., Meth. in Enzymol., 154, 350 (1987); Kunkel, T. A. et al., Meth. in Enzymol., 154, 367 (1987)). The activity for selectively sulfating keratan sulfate, that is, transferring a sulfate group from a sulfate group donor to C-6 position of galactose residue of keratan sulfate can be measured by, for example, an enzyme activity assay method to be described hereinafter, and those skilled in the art will readily identify such deletion, substitution or addition of one or more amino acids that substantially do not impair the activity.

The polypeptide of the present invention is preferably a polypeptide of KSGal6ST containing at least a part of the amino acid sequence shown in SEQ ID NO: 2 and not containing substitution, deletion or addition of the amino acids. More preferably, it is a polypeptide containing at least a part of the amino acid sequence represented by the amino acids 1–411 of SEQ ID NO: 2.

It is predicted that the amino acid sequence may be different between individuals. The polypeptide of the present invention include homologous variants having the differences.

The expression of "to comprise at least a part of an amino acid sequence" means to contain a minimum amino acid sequence sufficient for exhibiting the sulfotransferase activity for selectively sulfating keratan sulfate.

The polypeptide of the present invention may also be a polypeptide comprising a portion of the polypeptide mentioned above. The term "portion" herein used means a portion exhibiting some activity or having some function such as sulfotransferase activity and antigenicity. Such a portion can be readily identified by those skilled in the art.

The polypeptide of the present invention should not necessarily be constituted by only the polypeptide itself, and it may be in the form of fused polypeptide, if necessary. For example, a fusion polypeptide containing the peptide of the present invention and another polypeptide required for the expression, a fusion polypeptide containing the peptide of the present invention and glutathione-S-transferase, a fusion polypeptide containing the peptide of the present invention and a peptide to be biotinylated and the like can be exemplified, but it is not limited to these.

<2> Method for the production of the polypeptide of the present invention

The polypeptide of the present invention mentioned above can be obtained by using the DNA of the present invention described hereinafter. Namely, the polypeptide of the present invention can be produced by culturing cells harboring the DNA of the present invention in a suitable culture medium so that a polypeptide coded by the DNA is produced and accumulated in the culture, and collecting the polypeptide from the culture.

Cells harboring a DNA of the present invention can be obtained by inserting a fragment of the DNA of the present invention into a known expression vector to construct a recombinant plasmid, and transforming cells with the recombinant plasmid. The cells may be procaryotic cells such as E. coli or eucaryotic cells such as mammalian cells.

In this production method, any host-vector systems conventionally used for the production of proteins can be used and, for example, a combination of mammalian cells such as COS-7 cells and a vector for mammalian cell expression such as pCXN2 (Niwa, H., Yamamura, K. and Miyazaki, J. (1991) Gene 108, 193–200) or the like may be preferably employed. Culture medium and culture condition may be suitably selected depending on the host cells to be used.

The DNA of the present invention may be directly expressed, or may be expressed as a fusion polypeptide with another polypeptide. The DNA of the present invention may be expressed in its full length, or its part maybe expressed as a partial peptide.

The polypeptide of the present invention can be collected from culture by a known method for purification of polypeptides. The culture includes culture medium and cells contained in the medium.

Antibodies binding to KSGal6ST can be prepared by using a polypeptide of KSGal6ST, a partial polypeptide thereof or a fusion polypeptide thereof with another polypeptide prepared as above. The preparation of such antibodies can be carried out in a manner similar to that of the conventional preparation of antibodies. Monoclonal antibodies binding to KSGal6ST may also be prepared in a conventional manner.

<3> DNA of the present invention

The DNA of the present invention is a DNA coding for at least a part of the above polypeptide of keratan sulfate 6-sulfotransferase (KSGal6ST), and it is isolated from human for the first time according to the present invention.

Nucleotide sequence of the DNA of the present invention is not particularly limited so long as it codes for at least a part of the polypeptide of KSGal6ST.

The polypeptide of human KSGal6ST coded by the DNA of the present invention may contain deletion, substitution or addition of one or more amino acids that substantially does not impair the activity for selectively sulfating keratan sulfate.

As an example of the DNA of the present invention, a DNA having nucleotide sequence coding for the amino acid sequence represented by the amino acids 1–411 of SEQ ID NO: 2 can be mentioned, and such a DNA is preferred. Specifically, as an example of the DNA of the present invention, a DNA containing at least apart of the nucleotide sequence shown as SEQ ID NO: 1 can be mentioned, and such a DNA is particularly preferred. Specific examples of such a DNA include a DNA having a nucleotide sequence represented by nucleotides 1 to 1233 of SEQ ID NO: 1.

It will be readily understood by those skilled in the art that various DNAs having nucleotide sequences different from those exemplified above due to the degeneracy of genetic code may also be the DNA of the present invention. Any of such DNAs fall within the scope of the present invention.

Further, while it is expected that chromosome KSGal6ST gene contains introns in the coding region, such a DNA fragment interrupted with introns may be a DNA fragment of the present invention so long as it codes for at least a part of the polypeptide of KSGal6ST. That is, the expression of "code for" herein used may also mean to have a nucleotide sequence which may undergo processing during transcription and ultimately afford a desired polypeptide.

The expression of a "sequence coding for at least a part of polypeptide" herein used preferably means a sequence coding for a sequence exhibiting a certain activity or function such as the KSGal6ST activity and antigenicity, or a sequence containing a nucleotide sequence specific to that of KSGal6ST and hence usable as a primer or probe.

Any DNA or RNA complementary to the DNA of the present invention also falls within the scope of the present invention. Furthermore, the DNA of the present invention may be constituted by a single strand coding for KSGal6ST, or it may be a double stranded nucleic acid consisting of a DNA strand coding for KSGal6ST and another DNA or RNA strand complementary to the DNA strand.

The DNA of the present invention may contain the KSGal6ST coding region in its full length, or may contain a sequence coding for a part of the KSGal6ST peptide.

Because the nucleotide sequence of the DNA of the present invention has been elucidated by the present invention, it can be obtained by synthesizing it based on the elucidated sequence, or it can be obtained by amplifying it from human chromosome DNA or mRNA by PCR (polymerase chain reaction) technique using an oligonucleotide primer prepared based on the elucidated sequence. The DNA of the present invention was originally obtained by cDNA cloning process comprising the steps mentioned below as described in the examples hereinafter.

(1) Cloning of cDNA coding for polypeptide of chick chondroitin 6-sulfotransferase (C6ST)

① Sequencing of partial amino acid sequence of C6ST purified from chick embryo chondrocytes ② Preparation of oligonucleotide primer for PCR based on the amino acid sequence ③ Amplification of partial cDNA from poly (A)⁺ RNA of C6ST derived from chick embryo chondrocytes by PCR ④ Selection of full length C6ST cDNA from a cDNA library derived from chick embryo chondrocytes (2) Cloning of cDNA coding for polypeptide of human KSGal6ST ① Preparation of probe for screening of cDNA library based on the results of sequencing of the cDNA isolated in the above (1) ④

② Screening for cDNA clone coding for human KSGal6ST using the probe

③ Nucleotide sequencing of the screened cDNA

However, the preparation of the DNA of the present invention is not limited to the methods mentioned above, and the DNA of the present invention can be produced by PCR or any other known methods for cDNA cloning.

The method for obtaining the DNA of the present invention will be specifically explained hereinafter.

(1) Cloning of cDNA coding for polypeptide of chick C6ST

Cloning of cDNA coding for polypeptide of chick C6ST can be performed according to a known method. (Fukuta, M., Uchimura. K., Nakashima, K., Kato, M., Kimata, K., Shinomura, T., and Habuchi, O. (1995) J. Biol. Chem. 270, 18575–18580)

(2) Cloning of cDNA coding for polypeptide of human KSGal6ST

① Preparation of hybridization probe

A radioactive probe labeled with [$^{32}$P] dCTP for cDNA library screening can be obtained by the random primer labeling method using the cDNA of chick C6ST obtained as described above. That is, such a radioactively labeled DNA probe can be obtained by the random oligonucleotide-primed labeling method (Feinberg, A. P., and Vogelstein, B. (1983) Anal. Biochem. 132, 6–13) for the above chick cDNA using [$\alpha$-$^{32}$P] dCTP (Amersham) and DNA Random Labeling Kit (Takara Shuzo).

② Preparation of human cDNA library

A human CDNA library can be constructed by the preparation of total RNAs from human tissues or cells, preparation of poly(A)$^+$ RNAs from the total RNAs, and reverse transcription using the poly(A)$^+$ RNAs as templates. All of these process can be done by methods conventionally used in the field of genetic engineering.

Each cDNA is ligated to a cloning vector. Though the cloning vector is not particularly limited, for example, λgt11 digested with EcoRI is preferably used. Commercially available human cDNA ligated to a cloning vector may also be used. Specifically, human fetal brain cDNA library utilizing lambda vector, λgt11, available from Clontech is preferred.

③ Screening of cDNA clone coding for human KSGal6ST

Phage clones containing a full length KSGal6ST cDNA can be selected from the human cDNA library obtained as described above by hybridization utilizing the radioactive probe labeled with [$^{32}$P]dCTP prepared in the above ①. Hybridization can be performed by a conventional method used in the field of genetic engineering such as plaque hybridization. Positive clones can be selected as the plaques hybridized with the probe by detecting the labeling agent bound to the probe.

Phage DNA is prepared from the selected positive clones, and digested with an appropriate restriction enzyme to afford a cDNA fragment for insertion. This fragment is inserted into a suitable expression vector to construct a recombinant plasmid. Host cells suitable for the expression vector are transfected with the recombinant plasmid, and the cDNA is expressed in the host cell. Chondroitin 6-sulfotransferase activity, chondroitin 4-sulfotransferase activity and keratan sulfate sulfotransferase activity in the cells are measured, and cells exhibiting only the keratan sulfate sulfotransferase (KSST) activity are selected.

④ Nucleotide sequencing of cDNA

Among the selected positive clones, clones introduced into the cells strongly exhibiting only the KSST activity are used to prepare phage DNA, and KSGal6ST cDNA can be excised by using a suitable restriction enzyme from the phage DNA. The resulting cDNA can be sequenced as they are, or after subcloned into a suitable plasmid.

A nucleotide sequence of open reading frame of cDNA coding for human KSGal6ST, which was determined as described above, is shown as SEQ ID NO: 1 with the amino acid sequence therefor as SEQ ID NO: 2. A polypeptide constituted by 411 amino acid residues with a molecular weight of about 46,700 is predicted from a single open reading frame.

The DNA obtained as described above may have substitution, deletion or addition of a nucleotide, which may cause substitution, deletion or addition of one or more amino acid residues, so long as the activity for sulfating keratan sulfate of KSGal6ST coded by this DNA is not substantially impaired. Such substitution, deletion or addition of a nucleotide can be introduced into the DNA sequence by synthesizing a sequence containing restriction sites at its both ends and mutated sequence, and replacing a corresponding sequence of unmutated DNA sequence with the synthesized sequence. Furthermore, such substitution, deletion or addition can be introduced into a DNA sequence by the site-directed mutagenesis (Kramer, W. and Frits, H. J., Meth. in Enzymol., 154, 350 (1987); Kunkel, T. A. et.al., Meth. in Enzymol., 154, 367 (1987)). The activity for selectively sulfating keratan sulfate, i.e., the activity for selectively transferring a sulfate group from a sulfate group donor to the hydroxyl group at C-6 position of galactose residue of keratan sulfate can be measured by, for example, the enzyme activity assay method described hereinafter, and those skilled in the art will be able to readily identify substitution, deletion or addition of one or more amino acid residues which does not substantially impair the activity.

<4> Method for the production of sulfated polysaccharide

The method for producing a sulfated polysaccharide of the present invention is characterized in that it comprises exposing keratan sulfate to KSGal6ST which selectively sulfates keratan sulfate.

When keratan sulfate is placed under the activity of KSGal6ST in the presence of a sulfate group donor, sulfate groups are transferred to the hydroxyl groups at C-6 positions of galactose residues of keratan sulfate, and thus sulfated polysaccharides are formed. While pH value for this reaction is not particularly limited so long as the activity of the KSGal6ST is maintained, it is preferred that the reaction is performed under a pH condition around the optimum pH of the KSGal6ST. The reaction temperature for the reaction utilizing the KSGal6ST is not also particularly limited so long as the activity of the KSGal6ST is maintained, but it is preferred that the reaction should be performed at a temperature around the optimum temperature of the KSGal6ST. When an agent capable of enhancing the activity of the KSGal6ST is available, such an agent may be added to the reaction system. Reaction time can be suitably selected by those skilled in the art depending on amounts of keratan sulfate, the sulfate group donor and the KSGal6ST, and other reaction conditions. In general, the reaction is preferably performed at a temperature of around 37° C. and a pH value of about 6 to 7. Ca$^{2+}$ or Mn$^{2+}$ ions may be coexisted during the reaction.

As the sulfate group donor for the reaction utilizing the KSGal6ST, an active sulfate (3'-phosphoadenosine 5'-phosphosulfate, referred to as "PAPS" hereinafter) is preferred.

When the reaction is performed in a small scale, the KSGal6ST selectively sulfating keratan sulfate itself can be used with keratan sulfate and the sulfate group donor. When the reaction is performed in a large scale, the KSGal6ST immobilized on a suitable solid phase (e.g., beads) can be used, or the reaction system can be placed under continuous action of the enzyme by using a reactor of membrane type provided with a ultrafiltration membrane, dialysis membrane or the like. A bioreacter which recycles (synthesizes) the sulfate group donor can be used together.

In order to collect the sulfated polysaccharide from the reaction mixture, conventional methods for the separation and purification of polysaccharides can be used. For example, it can be performed by, adsorption chromatography, anion exchange chromatography, hydrophobic chromatography, gel filtration, gel permeation chromatography, paper electrophoresis, paper chromatography, fractionation with an organic solvent (for example, alcohols, acetone and the like are preferred) or a combination thereof. However, the separation and purification methods are not limited to these.

The substrate, keratan sulfate, is not also particularly limited, and those from various origins with various sulfation degrees and molecular weights can be used.

EXAMPLES

The present invention will be explained more specifically with reference to the following examples. However, these examples are only some embodiments of the present invention, and therefore the present invention is not limited by these examples. Techniques generally used in the examples will be described first. "%" means "% by weight" unless otherwise indicated.

Enzyme activity assay method

Sulfotransferase activity was assayed as follows.

The reaction mixtures for the assay of chondroitin sulfotransferase activity and keratan sulfate sulfotransferase activity had the following composition: 2.5 $\mu$mol of imidazole-hydrochloric acid (pH 6.8), 1.25 $\mu$g (for the chondroitin sulfotransferase activity assay) or 3.75 $\mu$g (for the keratan sulfate sulfotransferase activity assay) of protamine hydrochloride, 0.1 $\mu$mol of dithiothreitol, 25 nmol (as glucuronic acid) of chondroitin (for the chondroitin sulfotransferase activity assay) or 25 nmol (as glucosamine) of keratan sulfate (for the keratan sulfate sulfotransferase activity assay), 25 pmol of [$^{35}$S]PAPS (3'-phosphoadenosine 5'-phosphosulfate, about 2.5×10$^5$ cpm) and enzyme in a total volume of 50 $\mu$l (Reaction Mixture I).

Another reaction mixture for the assay of activity for various kinds of glycosaminoglycan had the following composition: 2.5 $\mu$mol of imidazole-hydrochloric acid (pH 6.8), 0.5 $\mu$g of CaCl$_2$, 0.1 $\mu$mol of dithiothreitol, 25 nmol (as glucosamine) of keratan sulfate, 25 pmol of [$^{35}$S]PAPS and enzyme in a total volume of 50 $\mu$l (Reaction Mixture II).

Activity for various kinds of glycosaminoglycans as the substrate was assayed by using 25 nmol (as galactosamine for chondroitin sulfate (A and C) and dermatan sulfate, and as glucosamine for keratan sulfate and CDSNS-heparin (completely desulfated, N-sulfated heparin, available from Seikagaku Corp.)) of glycosaminoglycan instead of keratan sulfate.

In the above both cases, the reaction mixtures were incubated at 37° C. for 20 minutes, and the reaction was stopped by immersing reaction tubes into boiling water for one minute.

After stopping the reaction, 0.1 $\mu$mol (as glucuronic acid) of chondroitin sulfate A was added as a carrier, and 3 volumes of ethanol containing 1.3% potassium acetate was added to the reaction mixture to precipitate $^{35}$S-labeled polysaccharide. The reaction mixture was centrifuged at 10,000×g for 10 minutes, and the resulting precipitates were dissolved in 70 $\mu$l of water. The resulting solution (50 $\mu$l) was loaded on a desalting column equilibrated with 0.1 M NH$_4$HCO$_3$, and the eluted fractions containing the $^{35}$S-labeled polysaccharide were collected. Scintillation cocktail (1 ml, Clearsol, Nakarai Tesque) was added to 200 $\mu$l of each of the obtained fractions, and incorporation of $^{35}$S into the polysaccharide was determined by assaying $^{35}$S-radioactivity. Activity catalyzing transfer of 1 pmol sulfate group/minute was defined as 1 unit.

When the chondroitin 6-sulfotransferase (C6ST) activity and the chondroitin 4-sulfotransferase (C4ST) activity were distinctively assayed, 400 $\mu$l of the remained solution was mixed with 800 $\mu$l of ethanol containing 1.3% potassium acetate. The mixture was placed on ice for 30 minutes, and then centrifuged at 10,000×g for ten minutes to precipitate the $^{35}$S-polysaccharide. The precipitates were dissolved in a buffer (25 $\mu$l) containing 0.1 mg/ml of BSA, 0.05 M Tris-acetic acid, pH 7.5, and 10 milliunits of chondroitinase ACII (derived from Arthrobacter aurescens, Seikagaku Corp.), and allowed to react at 37° C. for two hours. The reaction mixture was spotted on Whatman No. 1 filter paper together with 0.1 $\mu$mol each of 2-acetamido-2-deoxy-3-O-($\beta$-D-gluco-4-enopyranosyluronic acid)-6-O-sulfo-D-galactose ($\Delta$Di-6S) and 2-acetamido-2-deoxy-3-O-($\beta$D-gluco-4-enopyranosyluronic acid)-4-O-sulfo-D-galactose ($\Delta$Di-4S) (both from Seikagaku Corp.), and developed with 1-butanol/acetic acid/1 M ammonium hydroxide (2:3:1 (V/V/V)) for 20 hours.

Positions of $\Delta$Di-6S and $\Delta$Di-4S were determined by means of a ultraviolet lamp, and each site was cut out from the filter paper, and put into a scintillator prepared by dissolving 5 g of diphenyloxazole and 0.25 g of dimethyl 1,4-bis(2-(5-phenyloxazole))benzene in 1 L of toluene, and the radioactivity was measured. For the sample which was degraded with chondroitinase ACII, radioactivity remained at the starting point of the filter paper was 1% or less of the spotted radioactivity. Based on the incorporation of $^{35}$S into $\Delta$Di-6S and $\Delta$Di-4S, chondroitin 6-sulfotransferase activity and chondroitin 4-transferase activity were calculated.

Preparation example of a DNA of the present invention will be described hereinafter.

<1> Cloning of keratan sulfate 6-sulfotransferase cDNA (1) Preparation of hybridization probe A radioactive probe for cDNA library screening, which was labeled with [$^{32}$P]dCTP, was prepared by the random primer labeling method using the cDNA of chick C6ST derived from chick chondrocytes and obtained by a known method (J. Biol. Chem. 270 (31), 18575–18580, 1995). That is, a probe was obtained by radiolabeling the above chick cDNA in accordance with the random oligonucleotide-primed labeling method (Feinberg, A. P., and Vogelstein, B. (1983) Anal. Biochem. 132, 6–13) using [-$\alpha^{32}$P]dCTP (Amersham) and DNA Random Labeling Kit (Takara Shuzo).

(2) Human cDNA library

To obtain cDNA containing a full length coding region of human KSST, a human fetal brain cDNA library (Clontech) based on a lambda vector, $\lambda$gt11, was used.

cDNAs of this human fetal brain cDNA library were packaged into phage particles using an in vitro packaging kit (Gigapack II packaging extract, Stratagene). *Escherichia coli* Y1088 was infected with the resulting phage particles, and overlaid on a plate so that plaques was formed. The resulting phage library obtained as described above was used for cDNA screening without further amplification.

(3) Screening of KSST cDNA clones

Screening was performed for the plaques of λgt11 cDNA library obtained as described above. The plaques were transferred to a commercially available nylon membrane (Hybond N+ nylon membrane, Amersham), and the phage DNAs were fixed on the nylon membrane by the alkali fixation method. The fixed phage DNAs on the membrane were prehybridized in a solution containing 50% formamide, 5×SSPE (composition of 1×SSPE: 10 mM of $NaH_2PO_4$ (pH 7.4), 150 mM of NaCl, 1 mM of EDTA), 5×Denhardt's solution (composition of 1×Denhardt's solution: 0.02% of Ficoll 400, 0.02% of polyvinylpyrrolidone, 0.02% of BSA), 0.5% SDS, 0.04 mg/ml of denatured salmon sperm DNA, and 0.004 mg/ml of E. coli DNA at 42° C. for 3.5 hours. Hybridization was performed in the same solution as above except that it contained the $^{32}P$ labeled probe (prepared in the above <1>(1)) at 42° C. for 16 hours. Then, the membrane was washed with 1×SSPE, 0.1% SDS and then with 0.1×SSPE, 0.1% SDS at 55° C., and hybridization positive clones were detected by autoradiography. About 90 positive clones were obtained from $5 \times 10^5$ plaques.

(4) Preparation of expression plasmid

Positive λgt11 clones in the above hybridization were selected, and phage DNA was prepared for each clone, and cut with EcoRI, which can cut out a cDNA insert from the vector DNA as a single fragment. This cDNA fragment was inserted into the expression vector to construct a recombinant plasmid. As the expression vector, expression vector pCXN2 for mammalian cells (it was constructed by Dr. Jun'ichi Miyazaki of the University of Tokyo (Niwa, H., Yamamura, K., and Miyazaki, J. (1991) Gene 108, 193–200), obtained as a gift from Dr. Yasuhiro Hashimoto of The Tokyo Metropolitan Institute of Medical Science), was used. pCXN2 is a vector which contains streptomycin-resistant gene and penicillin-resistant gene, and can express a DNA fragment inserted in EcoRI site with the aid of β-actin gene promoter. Each cDNA fragment obtained from the above positive clones was ligated to the EcoRI site of pCXN2.

E. coli JM109 was transformed by using this ligation solution, and plated on a LB plate containing ampicillin. Recombinant plasmid was collected from the transformants, and purified by three times of CsCl/ethidium bromide density-gradient centrifugation.

(5) Transient expression of cDNA in COS-7 cells, and selection of cDNA which expresses sulfotransferase activity specific for keratan sulfate COS-7 cells were used as the host for the expression of cDNA. COS-7 cells (obtained from the RIKEN GENE BANK, Tsukuba, Japan) were inoculated on culture dishes having a diameter of 100 mm at a density of $8 \times 10^5$ cells/dish. Ten milliliters per culture dish of Dulbecco's Modified Eagle medium (DMEM) containing penicillin (100 units/ml), streptomycin (50 µg/ml) and 10% fetal bovine serum (Gibco BRL) was used as culture medium, and cultivation was carried out at 37° C. in 5 vol % of $CO_2$ and 95 vol % of air.

When the cell density reached $3 \times 10^6$ cells/dish (after 48 hours of cultivation), the COS-7 cells were transfected. Transfection was performed by the DEAE-dextran method (Aruffo, A. (1991) in Current Protocols in Molecular Biology, Suppl. 14, Unit 16.13, Greene Publishing Associates and Wiley Interscience, New York). Five milliliters of preliminarily heated DMEM containing 10% of Nu serum (serum substitute with a low protein concentration, Collaborative Biomedical Products) was mixed with 0.2 ml of PBS (phosphate buffered saline) containing 10 mg/ml DEAE-dextran and 2.5 mM Chloroquine solution. This solution was mixed with 15 µg of the recombinant plasmid, and the mixture was added to the cell suspension. After incubated the cells in a $CO_2$ incubator for four hours, the culture medium was substituted with 5 ml of PBS solution containing 10% dimethyl sulfoxide (DMSO). The cells were left at room temperature for two minutes, the dimethyl sulfoxide solution was removed by aspiration, and 25 ml of DMEM containing penicillin (100 units/ml), streptomycin (50 µg/ml) and 10% fetal bovine serum was added thereto. The cells were incubated for 67 hours, and then washed with DMEM alone. The cells were collected and homogenized in 1.5 ml of 0.25 M sucrose, 10 mM Tris-HCl (pH 7.2) and 0.5% Triton X-100 solution per cells from one dish by a Dounce homogenizer. The resulting homogenate was centrifuged at 10,000×g for 20 minutes, and chondroitin 6-sulfotransferase (C6ST) activity, chondroitin 4-sulfotransferase (C4ST) activity and keratan sulfate sulfotransferase (KSST) activity in the supernatant fraction were assayed by the activity assay method utilizing Reaction Mixture I. The reaction mixture was incubated at 37° C. for 20 minutes, and then the reaction was stopped by heating the reaction tube at 100° C. for one minute. Then, the produced $^{35}S$-labeled glycosaminoglycan was collected by ethanol precipitation, separated by gel chromatography utilizing a fast desalting column (Habuchi et al., J. Biol. Chem., 268 (29) 21968–21974, 1993), and its radioactivity was measured. As a result, it was found that, while C6ST and C4ST activities were not observed in the transfected cells, some of them exhibited strong KSST activity.

(6) Nucleotide sequencing of cDNA and deduced polypeptide

λgt11 clones which were positive in the hybridization and incorporated into the cells strongly exhibiting only the KSST activity were selected, each phage DNA was prepared therefrom and digested with EcoRI to excise cDNA insertion fragment as a single fragment. The resulting cDNA fragments were subcloned into Bluescript plasmid (Stratagene). Deletion clones were prepared by a known method (Henikoff, S. (1984) Gene 28, 351–359, Yanisch-Perron, C., Viera, J., and Messing, J. (1985) Gene 33, 103–109) using DNA deletion kit (Takara Shuzo). Both strands of the resulting deletion clones were independently sequenced by the dideoxy chain termination method (Sanger, F., Nicklens, S., and Coulson, A. R. (1977) Proc. Natl. Acad. Sci. U.S.A. 74, 5463–5467) using [α-$^{32}P$]dCTP and Sequenase (U.S. Biochemical). The determined DNA sequences were analyzed by Gene Works computer program (IntelliGenetics). The elucidated cDNA sequence of KSST and polypeptide sequence deduced from the sequence are shown in SEQ ID NO: 1. A single open reading frame suggests a polypeptide of 411 amino acid residues coded by the cDNA with a molecular weight of about 46700 and an isoelectric point of about 9.5 deduced from the amino acid sequence. This polypeptide also contained 5 positions susceptible to N-linked glycosylation. To determine whether this polypeptide possessed a transmembrane domain and, if it possessed, to locate the domain, a hydropathy plot was prepared from the deduced amino acid sequence. The hydropathy plot was calculated with a window of 11 amino acids according to the method of Kyte (Kyte, J. and Doolittle, R. F., (1982) J. Mol. Biol. 157, 105–132). Analysis of the plot revealed a distinctive hydrophobic domain of 12 amino acid residues at the amino terminus, which was considered as a transmembrane domain.

This cDNA was introduced into a plasmid (pCXN2) (a recombinant plasmid where the direction of the promoter is conformed with that of the cDNA was designated as pCXNKSST, and recombinant plasmid where the cDNA was inserted in a reversed direction was designated as pCXNKSST2), and COS-7 cells were transfected with the obtained plasmids by the method described above. Sixty seven hours after the transfection, the COS-7 cells were homogenized and centrifuged, and activities of C6ST, C4ST and KSST in the resulting supernatant were assayed according to the activity assay method utilizing Reaction Mixture I. As a result, as shown in Table 1, the cells incorporated with the vector inserted with the isolated cDNA of KSST in the correct direction exhibited 6- to 10-fold higher KSST activity compared with the control, whereas they exhibited no increase of the C6ST and C4ST activities. When dermatan sulfate, heparan sulfate, or completely desulfated, N-sulfated heparin (CDSNS-heparin) was used as the sulfate group receptor, no increase of sulfotransferase activity was observed.

TABLE 1

| Plasmid | Sulfotransferase activity (pmol/minute/mg protein) | | |
| --- | --- | --- | --- |
| | C6ST | C4ST | KSST |
| None (control) | 2.94 ± 0.23 | 0.44 ± 0.02 | 0.78 ± 0.20 |
| pCXNKSST | 2.90 ± 0.28 | 0.43 ± 0.06 | 6.73 ± 0.46 |
| pCXNKSST2 (control) | 2.91 ± 0.58 | 0.39 ± 0.14 | 1.14 ± 0.07 |

The values in Table 1 are an average of three determinations ± S.D.

<2> Preparation of keratan sulfate 6-sulfotransferase (1) Isolation of keratan sulfate 6-sulfotransferase A crude extract of COS-7 cells with pCXNKSST introduced, or COS-7 cells without pCXNKSST introduced (control) (4.8 mg as protein) was applied onto a DEAE-Sephacel column (Pharmacia, bed volume; 1 ml) equilibrated with 10 mM Tris-HCl buffer, pH 7.2, containing 20% glycerol, 20 mM $MgCl_2$, 2 mM $CaCl_2$ and 10 mM 2-mercaptoethanol (Buffer A). The column was washed with Buffer A containing 0.05 M NaCl, and absorbed fraction was eluted with Buffer A containing 0.5 M NaCl to collect 1-ml fractions. The KSST activity and chondroitin sulfotransferase (CST) activity of the eluted fractions of the extracts of COS-7 cells with pCXNKSST introduced and the control COS-7 cells were assayed by the activity assay method utilizing Reaction Mixture I. The results are shown in FIG. 1.

In FIG. 1, A and C are elution profiles of the extract of COS-7 cells with pCXNKSST introduced, and B and D are those of the extract of control COS-7 cells. A and B represent KSST activity, and C and D represent CST activity. The arrows in FIG. 1 represent the starting point of the elution with Buffer A containing 0.5 M NaCl.

When the extract of COS-7 cells with pCXNKSST introduced was used, about 20% of KSST activity was found in the fraction not absorbed to the column, and about 80% of KSST activity was found in the adsorbed fraction (fraction eluted by Buffer A containing 0.5 M NaCl) (FIG. 1, A). The CST activity was found only in the adsorbed fraction (FIG. 1, C). When the extract of COS-7 cells without pCXNKSST plasmid introduced was applied to the same column, no KSST activity was found in the non-adsorbed fraction (FIG. 1, B).

To obtain the fraction having KSST activity but not having CST activity from the extract of COS-7 cells with pCXNKSST introduced, KSST not having CST activity was isolated from the non-adsorbed fraction as follows.

Homogenate of COS-7 cells with pCXNKSST introduced from 80 dishes (224 mg as protein) was applied to a DEAE-Sephadex A-50 column (Pharmacia, 2.2×13 cm) equilibrated with Buffer A. The column was washed with 500 ml of Buffer A , and then the adsorbed fraction was eluted with Buffer A containing 0.5 M NaCl. About one third of keratan sulfate sulfotransferase activity was observed in the non-adsorbed fraction, whereas about two thirds of KSST activity and the whole CST activity were found in the adsorbed fraction (fraction eluted with Buffer A containing 0.5 M NaCl).

The fraction not adsorbed was pooled and applied to a Heparin-Sepharose CL-6B column (Pharmacia, 1.2×8.0 cm) equilibrated with Buffer A containing 0.15 M NaCl. The adsorbed fraction was eluted with Buffer A containing 0.5 M NaCl, and the eluate was dialyzed against Buffer A containing 50 mM NaCl. The dialysate was used as KSST not containing CST. The KSST activity was purified by 15 times after the Heparin-Sepharose CL-6B column purification. Table 2 presents the data of KSST enzyme activity of the crude extract and the partially purified product with respect to various kinds of receptors, which were assayed by the activity assay method utilizing Reaction Mixture II. For the activity assay, 25 nmol (as galactosamine for chondroitin, chondroitin sulfate A, chondroitin sulfate C and dermatan sulfate, and as glucosamine for keratan sulfate and CDSNS-heparin) of glycosaminoglycan was used instead of the keratan sulfate contained in the standard reaction mixture.

The sulfotransferase activity for transferring a sulfate group to chondroitin, CDSNS-heparin or the like was found in the crude extract, but it was reduced to 2% or less of the keratan sulfate sulfotransferase activity after the purification.

TABLE 2

| Glycosamino-glycan (Receptor) | Sulfotransferase activity (pmol/minute/mg protein × $10^{-2}$) | |
| --- | --- | --- |
| | Crude extract | Partially purified product |
| None | 0.002 | 0.01 |
| Keratan sulfate | 0.168 | 2.51 |
| Chondroitin | 0.016 | 0.03 |
| Chondroitin sulfate A | 0.009 | 0.03 |
| Chondroitin sulfate C | 0.005 | 0.02 |
| Dermatan sulfate | 0.005 | 0.02 |
| CDSNS-heparin | 0.109 | 0.05 |

(2) Characteristics of KSST

Characterization of the KSST partially purified as described above was performed. The optimum pH of this KSST was 6.2 to 6.5. When KSST activity was measured by changing the $CaCl_2$ used in the activity assay method utilizing Reaction Mixture II to various kinds of salts at a final concentration of 5 mM, $Mn^{2+}$ and $Ca^{2+}$ most strongly enhanced the KSST activity as shown in Table 3. The optimum concentration of $Ca^{2+}$ was about 10 mM. Dithiothreitol at a concentration up to 10 mM did not affect the KSST activity. Km value for PAPS was $2×10^{-7}$ M.

TABLE 3

| Added salt | Sulfotransferase activity (pmol/minute/mg protein) |
|---|---|
| None | 2.8 |
| Protamine Chloride | 8.8 |
| $MgCl_2$ | 18.8 |
| $CaCl_2$ | 26.2 |
| $SrCl_2$ | 21.6 |
| $BaCl_2$ | 21.0 |
| $MnCl_2$ | 28.0 |
| $FeSO_4$ | 3.0 |
| $CoCl_2$ | 24.6 |
| $NiCl_2$ | 10.0 |
| $ZnCl_2$ | 1.5 |
| $CuCl_2$ | 10.0 |

(3) Identification of position of sulfate group transferred by KSST

Figure 2:
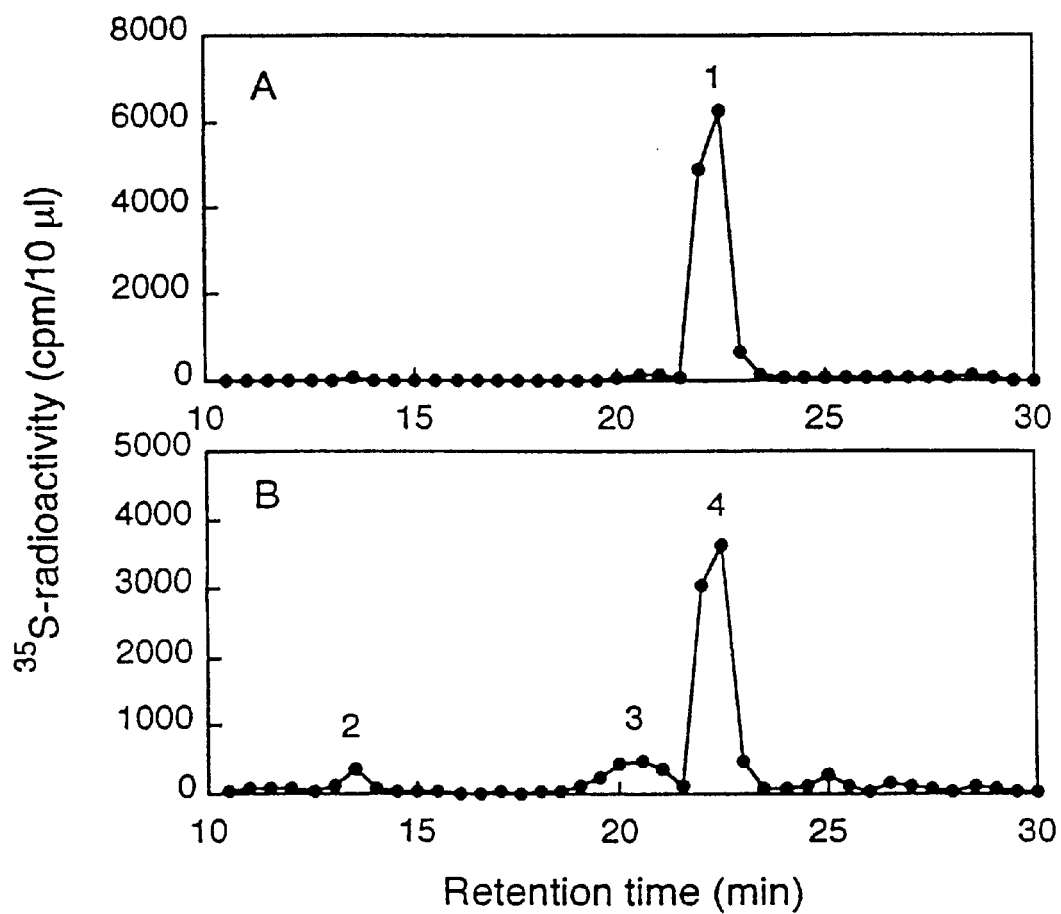
FIGS. 2A and 2B show the result of HPLC (Partisil 10-SAX) column chromatography of products obtained by degrading with keratanase II. A represents the elution profile of degraded products of keratan sulfate, and B represents that of degraded products of partially desulfated keratan sulfate.

Structural analysis of glycosaminoglycan synthesized from keratan sulfate by the partially purified KSST was performed. $^{35}$S-labeled glycosaminoglycan was prepared by incubating keratan sulfate, [$^{35}$S]PAPS and the partially purified KSST (2 μg of protein) in Reaction Mixture II. $^{35}$S-labeled glycosaminoglycan obtained from four reaction tubes was pooled. This glycosaminoglycan was separated from $^{35}SO_4$ and [$^{35}$S]PAPS using a fast desalting column, and lyophilized. The resulting sample was degraded with keratanase II (Seikagaku Corp.) as follows. Specifically, the sample was degraded in 50 μl of 2.5 μmol acetic acid buffer (pH 6.5) containing 0.005 unit of keratanase II, and the reaction mixture was incubated at 37° C. for 24 hours. The keratanase II degraded product was analyzed by HPLC using Whatman Partisil 10-SAX column (Whatman, 4.5×25 cm) equilibrated with 5 mM $KH_2PO_4$. The column was developed with 5 mM $KH_2PO_4$ for five minutes, and eluted with a gradient of 5 mM to 250 mM $KH_2PO_4$ over 20 minutes at a flow rate of 1 ml/min to collect 0.5-ml fractions, and $^{35}$S-radioactivity was then measured (FIG. 2, A). A single peak corresponding to Gal(6SO$_4$) β1-4GlcNAc (6SO$_4$) having $^{35}$S-radioactivity was obtained (FIG. 2, peak 1). The radioactive peak was collected, dried on a vacuum centrifugal evaporator, dissolved in a small amount of water, and injected into a Hiload Superdex 30 16/60 column (Pharmacia) equilibrated with 0.2 M $NH_4HCO_3$. Fractionation was performed at a flow rate of 1 ml/min to collect 1-ml fractions, each of which was mixed with 4 ml of Clearsol (Nakarai Tesque) and $^{35}$S-radioactivity was measured. Disaccharide was monitored by absorption at 210 nm. The resulting eluate was lyophilized.

The $^{35}$S-radioactive substance contained in Peak 1 in FIG. 2 was reduced with NaBH$_4$ and hydrolyzed with 50 μl of 0.1 M HCl at 100° C. for 40 minutes. The hydrolysate was purified by paper chromatography and paper electrophoresis. Specifically, the paper chromatography was performed by using Whatman No. 3 filter paper (2.5 cm×57 cm) and developing with 1-butanol/acetic acid/1 M NH$_3$ (3:2:1 (V/V/V)). The paper electrophoresis was performed by using Whatman No. 3 filter paper (2.5 cm×57 cm) which was immersed in a mixture of pyridine/acetic acid/water (1:10:400 (V/V/V), pH 4) at 30 V/cm for 40 minutes. After the paper electrophoresis and the paper chromatography, the filter paper was dried and cut into 1.25 cm pieces for each lane, and radioactivity was measured in a scintillation solution containing 5 g of diphenyloxazole and 0.25 g of dimethyl 1,4-bis(2-(5-phenyloxazole))benzene in 1 L of toluene. Peaks with small migration was collected and eluted to recover a mixture of Galβ1-4GlcNAc$_R$(6SO$_4$), Gal(6SO$_4$)β1-4GlcNAc$_R$ and Gal(6SO$_4$). This was mixed with Na$_2$CO$_3$ containing 0.5 M NaBH$_4$ (pH 10.2, 10 μl), and reduced on ice for two hours. Na$_2$CO$_3$ containing 0.5 M NaBH$_4$ (pH 10.2, 10 μl) was added thereto again, and incubated on ice for additional two hours. Excess NaBH$_4$ was decomposed by adding 3 M acetic acid (10 μl), and the residue was dried under nitrogen flow. The reduced product was dissolved in water, and applied onto a Dowex 50H$^+$ column (Daw Chemical). The eluate was dried, mixed with methanol, and the methanol was evaporated. Mixing and drying of methanol was repeated three times.

Figure 3:
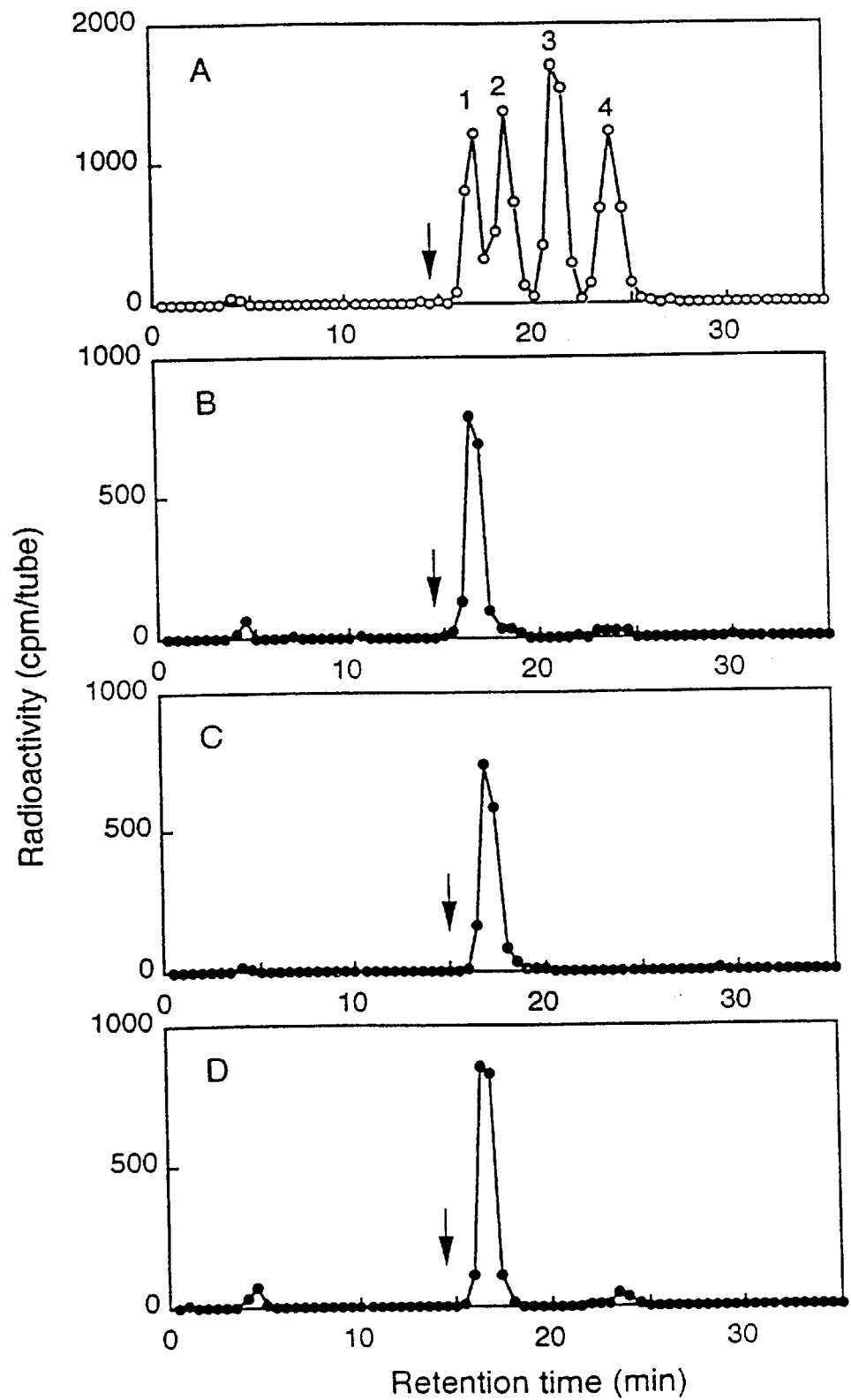
FIGS. 3A–3D show the result of HPLC column chromatography of hydrolysates obtained with keratanase II. A is the elution profile of $^3$H-labeled Gal(6SO$_4$)β1-4GlcNAc$_R$ (peak 1), Galβ1-4GlcNAc$_R$(6SO$_4$) (peak 2), GlcNAc$_R$ (6SO$_4$) (peak 3) and Gal$_R$(6SO$_4$) (peak 4). B represents the elution profile of the peak 1 of FIG. 2, A, C represents the peak 2 of FIG. 2, B, and D represents the peak 4 of FIG. 2, B, respectively. ○ represents $^3$H radioactivity, and • represents $^{35}$S-radioactivity.

The $^{35}$S-labeled substance migrated during the above operation to a position corresponding to Galβ1-4GlcNAc$_R$ (6SO$_4$) wherein R means alditol formed by the reduction with NaBH$_4$ was subjected to HPLC to separate into Gal (6SO$_4$)β1-4GlcNAc$_R$ and Galβ1-4GlcNAc$_R$ (6SO$_4$) (FIG. 3, B). Specifically, a sample was applied on a Whatman Partisil 10-SAX column (4.5×25 cm) equilibrated with 5 mM $KH_2PO_4$, and developed with 5 mM $KH_2PO_4$ at a flow rate of 1 ml/min and a column temperature of 40° C. 0.5-ml fractions were collected, each was mixed with 4 ml of Clearsol, and radioactivity was measured. As a result, strong $^{35}$S-radioactivity was detected at a position corresponding to Gal(6SO$_4$)β1-4GlcNAc$_R$, and weak radioactivity was detected at a position of Gal$_R$(6SO$_4$). Any radioactivity was not detected at a position corresponding to Galβ1-4GlcNAc$_R$(6SO$_4$). This suggests that KSST transfers sulfate groups to monosulfated repetition units of keratan sulfate, i.e., C-6 position of galactose residues contained in a structure composed of the repetition unit Galβ1-4GlcNAc(6SO$_4$). To determine whether the enzyme can transfer the group to galactose residues of the repetition unit not having a sulfate group of keratan sulfate, the activity assay method utilizing Reaction Mixture II was performed by using partially desulfated keratan sulfate as receptor of sulfate groups with incubation of 18 hours. The $^{35}$S-labeled glycosaminoglycan produced from the desulfated keratan sulfate was degraded with 0.005 unit of keratanase II, and the degraded product was subjected to HPLC utilizing Whatman Partisil 10-SAX column (4.5×25 cm) equilibrated with 5 mM $KH_2PO_4$, which was developed at a flow rate of 1 ml/min for 5 minutes, and eluted with a gradient of 5 mM to 250 mM of $KH_2PO_4$ over 20 minutes at a flow rate of 1 ml/min as described above. 0.5-ml fractions were collected to obtain three radioactive peaks (FIG. 2, B). Peak 2 in FIG. 2, B was eluted a little earlier than Galβ1-4GlcNAc(6SO$_4$), and Peak 4 was eluted at the location of Gal(6SO$_4$)β1-4GlcNAc (6SO$_4$). Peak 3 was eluted between Peak 2 and Peak 4.

Peak 2 and Peak 4 of FIG. 2, B were similarly analyzed as the above Peak 1 of FIG. 2, and, as a result, a single peak was observed at the position of Gal(6SO$_4$)β1-4GlcNAc$_R$ (the results of the analysis of Peak 2 in FIG. 2 are shown in FIG. 3, C, and those for Peak 4 in FIG. 2 are shown in FIG. 3, D). These results clearly demonstrate that the enzyme transfers sulfate groups to C-6 positions of galactose residues bound to GlcNAc(6SO$_4$) or GlcNAc. Based on this fact, the enzyme of the present invention was named keratan sulfate galactose 6-sulfotransferase (KSGal6ST)

<3> Northern hybridization of poly A$^+$ RNA

Poly(A)$^+$ RNA extracted from various human tissues was denatured with 20 mM MOPS buffer, pH 7.0, containing 50% formamide (V/V) and 5% formaldehyde (V/V), and subjected to electrophoresis on 1.2% agarose gel containing 5% formaldehyde. It was transferred to a Hybond N$^+$ nylon membrane overnight. The RNA was fixed by heating to 80° C. for two hours, and prehybridized in a solution containing 50% formamide, 5×SSPE, 5×Denhardt's solution, 0.5% SDS and 0.1 mg/ml denatured salmon sperm DNA at 42° C. for three hours. Hybridization was performed at 42° C. for 14 hours using the above buffer containing a probe prepared by using $^{32}$P-labeled KSGal6ST cDNA prepared by the random oligonucleotide-primed labeling method. After the hybridization, the membrane was washed with 2×SSPE and 0.1% SDS at 65° C., and then with 1×SSPE and 0.1% SDS. An X-ray film was exposed to the membrane using an intensifying screen at −80° C. for 26 hours. As a result, when poly(A)$^+$ RNA of brain was used, a hybridization band was observed around 2.8 kb.

Expression of KSGal6ST in cornea was also examined by cross hybridization. Specifically, poly(A)$^+$ RNA from chick embryo cornea was prepared instead of the above poly(A)$^+$ RNA extracted from human tissues, and cross hybridization was performed by using a probe prepared from human KSGal6ST cDNA according to the method described above. Poly(A)$^+$ RNAs extracted from heart and brain of chick embryo were used as control. The poly(A)$^+$ RNA prepared from cornea of chick embryo showed a cross hybridization band.

What is claimed is:

1. A preparation comprising an isolated polypeptide of keratan sulfate 6-sulfotransferase, said preparation lacking any substantial N-acetylglucosamine-6-sulfotransferase activity, and said polypeptide having the following physicochemical properties:

(1) action: a sulfate group is transferred from a sulfate group donor to the hydroxyl group at C-6 position of galactose residue of keratan sulfate;

(2) substrate specificity: a sulfate group is not substantially transferred to chondroitin, chondroitin sulfate A, chondroitin sulfate C, dermatan sulfate and CDSNS-heparin;

(3) optimum pH: 6.2 to 6.5;

(4) activation: the stated action is increased by $Mn^{2+}$ or $Ca^{2+}$ (5) Km value for 3'-phosphoadenosine 5'-phosphosulfate: about $2\times10^{-7}$ M, said polypeptide being derived from human.

2. A preparation comprising an isolated polypeptide according to claim 1, which has the amino acid sequence represented as SEQ ID NO: 2.

3. A fusion polypeptide comprising the polypeptide as defined in claim 1 and another polypeptide.

4. A preparation comprising an isolated polypeptide of keratan sulfate 6-sulfotransferase, said polypeptide having the following physicochemical properties:

action: a sulfate group is transferred from a sulfate group donor to the hydroxyl group at the C-6 position of a galactose residue of keratan sulfate, and substrate specificity: a sulfate group is not substantially transferred to chondroitin, chondroitin sulfate A, chondroitin sulfate C, dennatan sulfate and CDSNS-heparin, said polypeptide being encoded by a cDNA of human keratan sulfate sulfotransferase (KSST) obtainable from a human cDNA library by using, as a probe, cDNA of chick chondroitin 6-sulfotransferase (C6ST) derived from chick chondrocytes under conditions in which hybridization is conducted at 42° C. in a solution containing 50% formamide, 5X SSPE, 5X Denhardt's solution, 0.5% SDS, 0.04 mg/mg/ml denatured salmon sperm DNA and 0.004 mg/mg/ml E. coli DNA and washing is conducted at 55° C. with 1X SSPE, 0.1% SDS and then with 0.1X SSPE, 0.1% SDS, said polypeptide having at least part of the amino acid sequence shown as SEQ ID No: 2, which may include a deletion, substitution or addition of one or more amino acids which substantially does not impair the stated activity of keratan sulfate 6-sulfotransferase.

5. A preparation comprising an isolated polypeptide according to claim 4, which further has the following physicochemical properties:

optimum pH: 6.2–6.5;

activation: the stated action is increased by $Mn^{2+}$ or $Ca^{2+}$; and

Km value for 3'-phosphoadenosine 5'- phosphosulfate: about $2\times10^{-7}$ M.

6. A method for producing a sulfated polysaccharide comprising exposing keratan sulfate to the polypeptide of 6-sulfotransferase as defined in claim 1.

7. A method for producing a sulfated polysaccharide comprising exposing keratan sulfate to the polypeptide of 6-sulfotransferase as defined in claim 2.

8. A method for producing a sulfated polysaccharide comprising exposing keratan sulfate to the polypeptide of 6-sulfotransferase as defined in claim 4.

* * * * *